(12) United States Patent
Lonien et al.

(10) Patent No.: US 10,293,115 B2
(45) Date of Patent: May 21, 2019

(54) INJECTOR FOR ADMINISTERING A LIQUID OR PASTY SUBSTANCE, IN PARTICULAR A DRUG

(71) Applicant: elm-plastic GmbH, Dudeldorf (DE)

(72) Inventors: Birgit Lonien, Dudeldorf (DE); Sascha Moehs, Dudeldorf (DE)

(73) Assignee: elm-plastic GmbH, Dudeldorf (DE)

( * ) Notice: Subject to any disclaimer, the term of this patent is extended or adjusted under 35 U.S.C. 154(b) by 0 days.

(21) Appl. No.: 14/940,466

(22) Filed: Nov. 13, 2015

(65) Prior Publication Data
US 2016/0158457 A1    Jun. 9, 2016

(30) Foreign Application Priority Data

Dec. 5, 2014  (DE) .......................... 10 2014 018 077
Feb. 19, 2015  (DE) .......................... 10 2015 002 234
Jul. 7, 2015  (EP) ..................................... 15175696

(51) Int. Cl.
| | |
|---|---|
| *A61M 5/315* | (2006.01) |
| *A61M 5/19* | (2006.01) |
| *A61D 7/00* | (2006.01) |
| *A61D 1/02* | (2006.01) |
| *A61M 5/31* | (2006.01) |

(52) U.S. Cl.
CPC ........... *A61M 5/31596* (2013.01); *A61D 1/02* (2013.01); *A61D 7/00* (2013.01); *A61M 5/19* (2013.01); *A61M 2005/3103* (2013.01); *A61M 2005/31598* (2013.01)

(58) Field of Classification Search
CPC ........... A61M 2005/1787; A61M 2005/31598; A61M 5/284

USPC ......................................................... 604/191
See application file for complete search history.

(56) References Cited

U.S. PATENT DOCUMENTS

| | | | |
|---|---|---|---|
| 2,157,503 A | 5/1939 | Smith | |
| 3,659,749 A | 5/1972 | Schwartz | |
| 4,702,737 A | 10/1987 | Pizzino | |
| (Continued) | | | |

FOREIGN PATENT DOCUMENTS

| | | |
|---|---|---|
| CN | 1980614 A | 6/2007 |
| CN | 101175519 A | 5/2008 |
| (Continued) | | |

OTHER PUBLICATIONS

ISA European Patent Office, International Search Report Issued in Application No. PCT/IE2005/000007, dated May 18, 2005, WIPO, 4 pages.

(Continued)

*Primary Examiner* — Rebecca E Eisenberg
*Assistant Examiner* — John A Doubrava
(74) *Attorney, Agent, or Firm* — McCoy Russell LLP

(57) ABSTRACT

An injector for administering a first and a second liquid or pasty substance, in particular a drug, comprises an outer injector body in which an inner injector body is longitudinally displaceably guided in which a plunger is longitudinally displaceably guided. To improve such an injector, the inner injector body has a cuff which sealingly contacts the inner wall of the outer injector body and which can be flowed around by the second liquid or pasty substance when it is in the end position in the outer injector body.

14 Claims, 11 Drawing Sheets

(56) References Cited

U.S. PATENT DOCUMENTS

| | | | |
|---|---|---|---|
| 8,152,778 B2* | 4/2012 | Chebator | A61M 5/19 604/191 |
| 2003/0167041 A1* | 9/2003 | Rosoff | A61M 5/282 604/232 |
| 2005/0171506 A1* | 8/2005 | Hallahan | A61D 1/02 604/514 |
| 2009/0105660 A1* | 4/2009 | Muta | A61M 5/284 604/191 |
| 2010/0082015 A1* | 4/2010 | Chebator | A61M 5/19 604/533 |
| 2014/0276442 A1* | 9/2014 | Haughey | A61M 5/31596 604/191 |

FOREIGN PATENT DOCUMENTS

| | | |
|---|---|---|
| CN | 101394880 A | 3/2009 |
| CN | 101559247 A | 10/2009 |
| CN | 101716386 A | 6/2010 |
| CN | 101868274 A | 10/2010 |
| DE | 210386 A3 | 6/1984 |
| DE | 69531774 T2 | 7/2004 |
| DE | 102013112521 A1 | 5/2015 |
| EP | 0654280 A1 | 5/1995 |
| EP | 1093826 A1 | 4/2001 |
| WO | 9521639 A1 | 8/1995 |
| WO | 0211793 A1 | 2/2002 |
| WO | 02076534 A1 | 10/2002 |
| WO | 03022245 A1 | 3/2003 |
| WO | 2004039434 A2 | 5/2004 |
| WO | WO 2013/021186 A1 * | 2/2013 ............ A61M 5/315 |

OTHER PUBLICATIONS

State Intellectual Property Office of the People's Republic of China, Office Action and Search Report Issued in Application No. 201510836467.4, dated Jun. 26, 2018, 18 pages. (Submitted with Partial Translation).

* cited by examiner

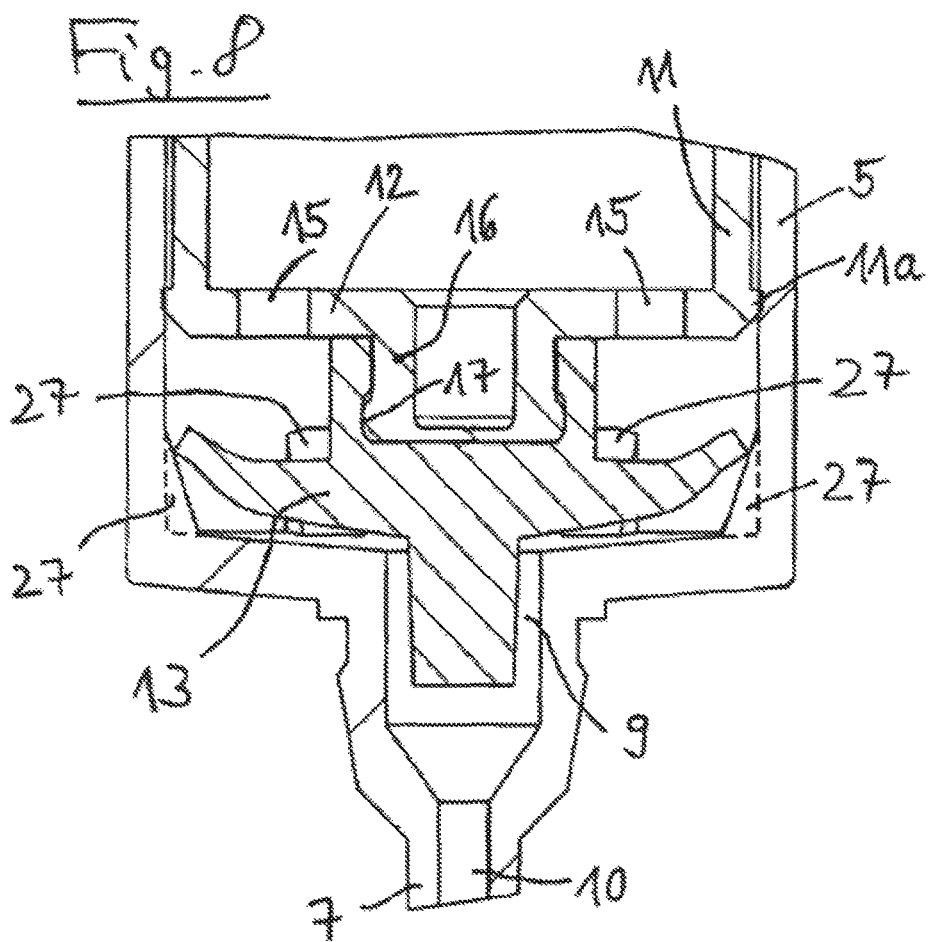
Fig. 8
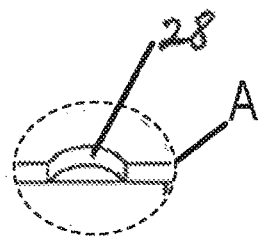
Webs serve as an abutment

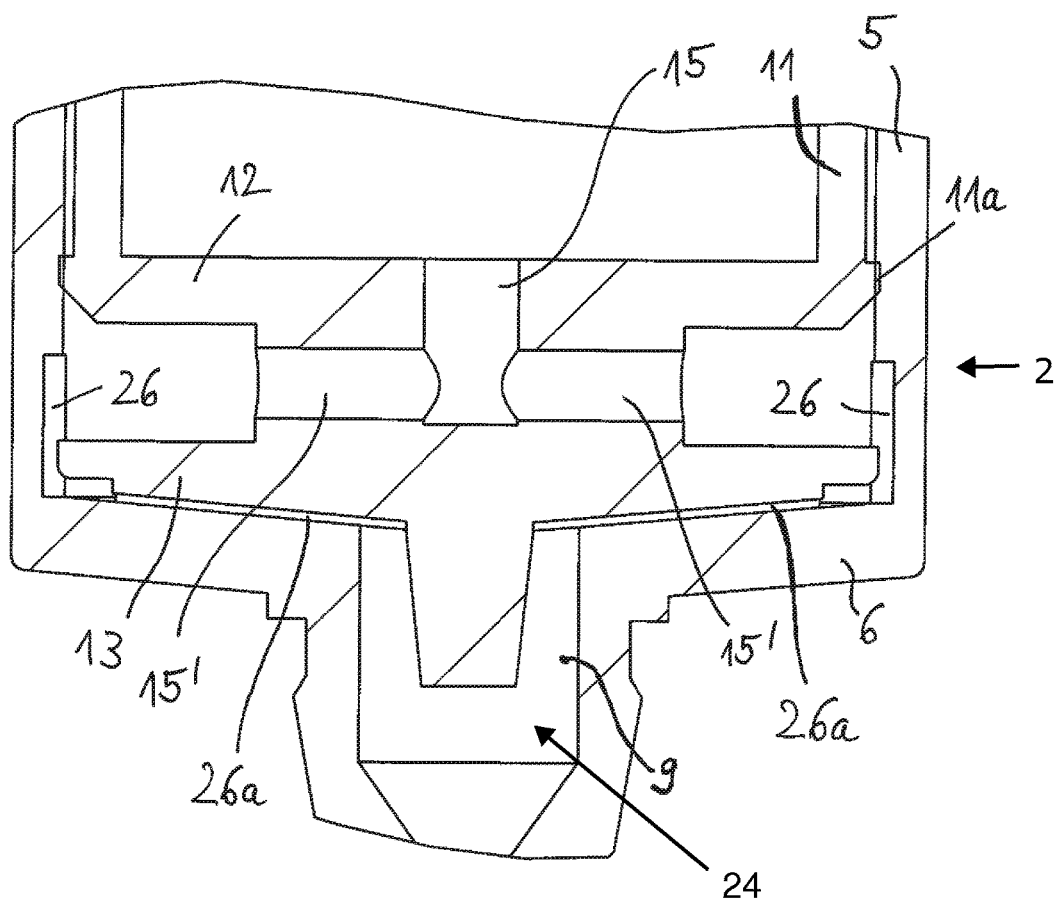

INJECTOR FOR ADMINISTERING A LIQUID OR PASTY SUBSTANCE, IN PARTICULAR A DRUG

CROSS REFERENCE TO RELATED APPLICATIONS

This application claims priority to German Patent Application No. 10 2014 018 077.8. entitled "Injector for Admisitering a Liquid or Pasty Substance, in Particular a Drug," filed on Dec. 5, 2014, and German Patent Application No. 10 2015 002 234.2, filed on Feb. 19, 2015, and also claims priority to European Patent Application No. 15175696, filed on Jul. 7, 2015, the entire contents of each of which are hereby incorporated by reference in their entirety for all purposes.

TECHNICAL FIELD

The present disclosure relates to an injector for administering a first or a second liquid or pasty substance. The first and/or second liquid or pasty substance can in particular be a drug or a substance containing one or more drugs.

BACKGROUND AND SUMMARY

The injector comprises an outer injector body, an inner injector body and a plunger. A first volume for the first liquid or pasty substance is formed in the outer injector body. A second volume for the second liquid or pasty substance is formed in the inner injector body. The inner injector body is longitudinally displaceably guided in the outer injector body. It can there be longitudinally guided in a rotatable or non-rotatable manner. The plunger is longitudinally displaceable guided in the inner injector body. It can there be longitudinally guided in a rotatable or non-rotatable manner.

The inner injector body is first moved in the outer injector body by a movement of the plunger. The first liquid or pasty substance is hereby administered through an opening in the region of the base wall of the outer injector body. When the inner injector body has reached its end position in the outer injector body, the plunger can be moved in the inner injector body. The second liquid or pasty substance can then be administered.

An injector in accordance with the preamble of claim 1 is known from DD 210 386 B.

U.S. Pat. No. 2,157,503 discloses a syringe into which an ampoule filled with liquid can be introduced. A tablet containing a medical preparation can be mixed with the liquid of the ampoule.

A blood removal and blood isolation system is known from DE 695 31 774 T2 which comprises a syringe cylinder, main piston and a divider piston.

It is the object of the present disclosure to provide an improved injector of the initially named type.

This object is achieved in accordance with the present disclosure by the features of claim 1. The inner injector has a cuff which sealingly contacts the inner wall of the outer injector body. The cuff in particular sealingly contacts the inner wall of the outer injector body during the movement of the inner injector body in the outer injector body. When the cuff is in the end position in the outer injector body, it can be flowed around by the second liquid or pasty substance. It is thereby ensured that the second liquid or pasty substance can also be administered after the administration of the first liquid or pasty substance.

Advantageous further developments of the present disclosure are described in the dependent claims.

It is advantageous if the outer injector body has one or more channels in its end region. The channel or channels can be located in the inner wall of the end region of the outer injector body. The second liquid or pasty substance can flow around the cuff when the cuff is in the end position in the outer injector body in that the second liquid or pasty substance flows through the channel or channels.

The cuff can have one or more grooves at its lower side. The second liquid or pasty substance can flow through these grooves when the cuff is in the end position in the outer injector body.

A further advantageous further development wherein the cuff is deformed in a manner in which it can be flowed around when it is in the end position in the outer injector body. Channels can be formed by the deformation of the cuff which are flowed through by the second liquid or pasty substance when the cuff is in the end position in the outer injector body.

It is advantageous if webs are provided in the end region of the outer injector body. The webs may be provided in the base wall of the outer injector body. The cuff can be deformed by the webs. The second liquid or pasty substance can flow through the regions between the webs. It is advantageous if more than two webs are present. The webs may be evenly distributed over the periphery.

The injector in accordance with the present disclosure can be used for administering one or more liquids and/or one or more pastes and/or one or more drugs into an udder of an animal. It can therefore in particular be used as an udder injector.

It is advantageous for the cuff to be releasably connected to the inner injector body.

It can, however, also be advantageous for the cuff to be formed in one piece with the inner injector body.

In accordance with a further advantageous further development, one or more channels are provided in the inner injector body, for example in its base wall.

The channel or channels can extend at least partially in a radial direction.

Embodiments of the present disclosure will be explained in detail in the following with reference to the enclosed figures.

BRIEF DESCRIPTION OF THE FIGURES

FIG. 8 shows an enlarged detail from FIG. 7.

FIG. 11 shows a modification of the embodiment in accordance with FIGS. 9 and 10 in which the channels extend partially in a radial direction in the inner injector body.

DETAILED DESCRIPTION

Figure 1:
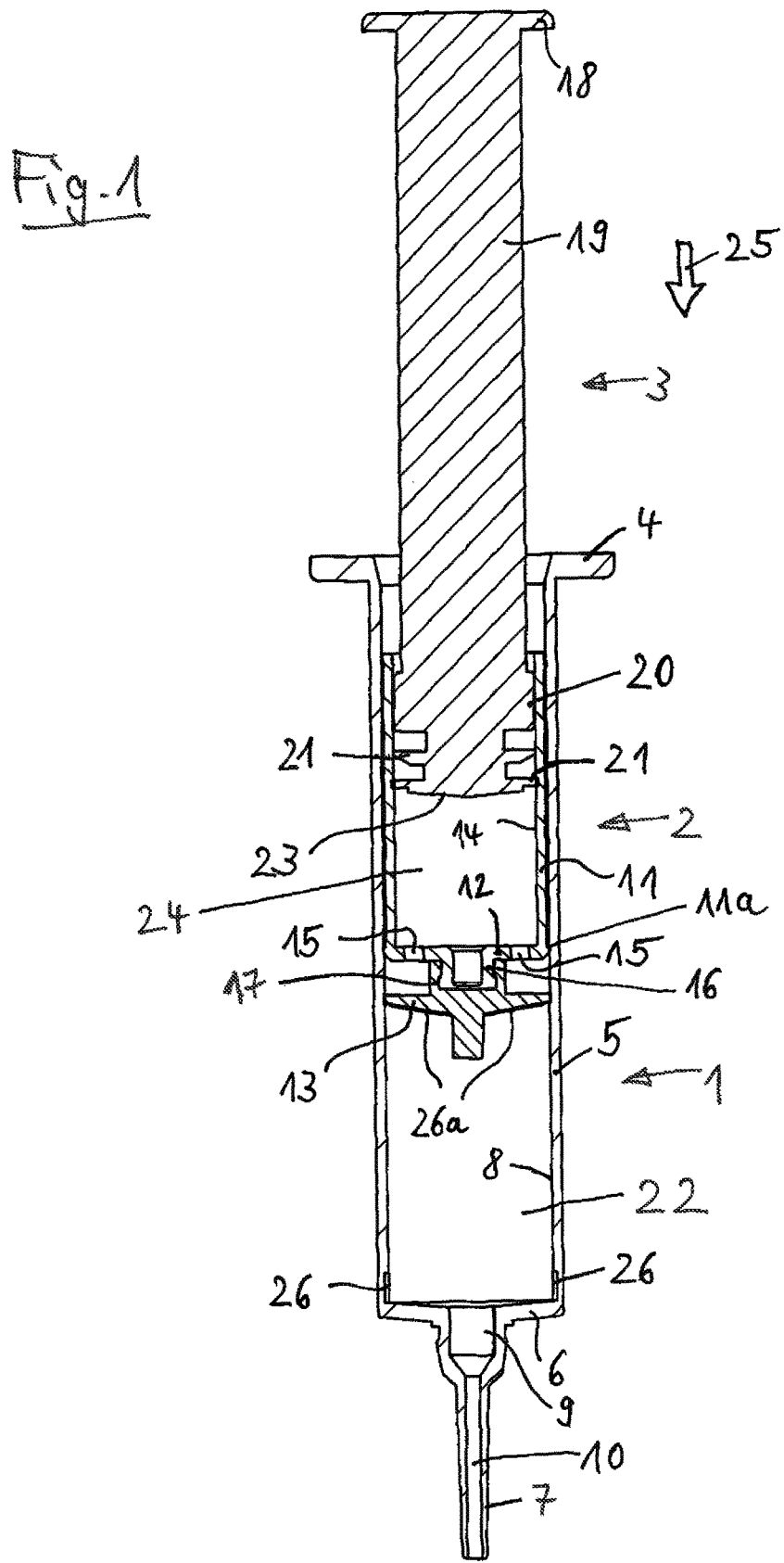
FIG. 1 shows a first embodiment of the present disclosure in the starting position in a lateral sectional view.

The first embodiment of the injector in accordance with the present disclosure shown in FIGS. 1 to 4 comprises an outer injector body 1, an inner injector body 2 and a plunger 3. The outer injector body 1 comprises an upper margin 4, which is outwardly directed, a jacket part 5, a base wall 6, and an administration spout 7. The jacket part 5 is cylindrical. It has an inner wall 8 along which the inner injector body 2 is longitudinally displaceably guided. The base wall 6 has an administration opening 9 at its center, the administration opening being connected to an administration channel 10 in the administration spout 7. The outer injector body 1 is formed in one piece.

The inner injector body 2 comprises a jacket part 11, a base wall 12, and a cuff 13. The jacket part 11 is cylindrical. Its outer wall is longitudinally displaceably guided along the inner wall 8 of the jacket part 5 of the outer injector body 1. For this purpose, the jacket part 11 has a sealing surface 11a at its lower end, with the diameter of said sealing surface being larger than the remaining diameter of the jacket part 11. The sealing surface 11a contacts the inner wall 8. The main function of the sealing surface 11a comprises ensuring a seal. It furthermore also satisfies a guiding function.

The jacket part 11 has an inner wall 14 in which the plunger 3 is longitudinally displaceably guided. Channels 15 are present in the base wall 12 of the inner injector body 2. The channels 15 are evenly distributed over the periphery.

The base wall 12 has at its lower side, which faces the base wall 6 of the outer injector body 1, a projection 16 onto which the cuff 13 is plugged. The cuff 13 is releasably connected to the projection 16 in this manner. The projection 16 has a bead 17 which is larger in diameter in its lower end region which faces the base wall 6 of the outer injector body 1. The bead 17 is outwardly rounded. The jacket part 11, the base wall 12, and the projection 16 of the inner injector body 2 are formed in one piece.

The plunger 3 comprises an upper margin 18, which is outwardly directed, a plunger body 19, a guide surface 20, and seals 21. The plunger body 19 has a cruciform cross-section. It can, however, also be configured in a different manner and can in particular be cylindrical. The diameter of the inner wall 14 of the jacket part 11 of the inner injector body 2 is larger than the outer diameter of the plunger body 19. The guide surface 20 of the plunger 3 contacts the inner wall 14 of the jacket part 11 of the inner injector body 2. It is guided at the inner wall 14. The seals 21 sealingly contact the inner wall 14 of the jacket part 11 of the inner injector body 2. The lower seal 21, which faces the base wall 12 of the inner injector body 2, has a larger diameter than the upper seal 21 which faces the upper margin 18 of the plunger 3. The lower seal 21 forms the main seal; the upper seal 21 forms an additional seal.

In operation, the injector is first located in the position shown in FIG. 1. The cuff 13 of the inner injector body 2 is spaced apart from the base wall 6 of the outer injector body 1. A first volume 22 for the first liquid or pasty substance is hereby formed. The lower end surface 23 of the plunger 3 is spaced apart from the base wall 12 of the inner injector body 2. A second volume 24 for the second liquid or pasty substance is hereby formed.

The plunger 3 is moved downwardly in the direction of the arrow 25 at the start of the administration process. In this respect, the plunger 3 and the inner injector body 2 are moved downwardly together with respect to the outer injector body 1. The volume 24, the channels 26, and the annular space between the base wall 12 of the inner injector body 2 and the cuff 13 form a space which is sealed overall and which is sealed by the seals 21 and the cuff 13. It is ensured by this space sealed overall that first the unit formed by the plunger 3 and the inner injector 2 is moved downwardly with respect to the outer injector body 1.

The plunger 3 and the inner injector body 2 are therefore moved downwardly together with respect to the outer injector body 1. The cuff 13 hereby moves toward the base wall 6 of the outer injector body 1, whereby the first volume 22 is reduced in size and the first liquid or pasty substance located therein is pressed out through the administration opening 9 and the administration channel 10.

Figure 2:
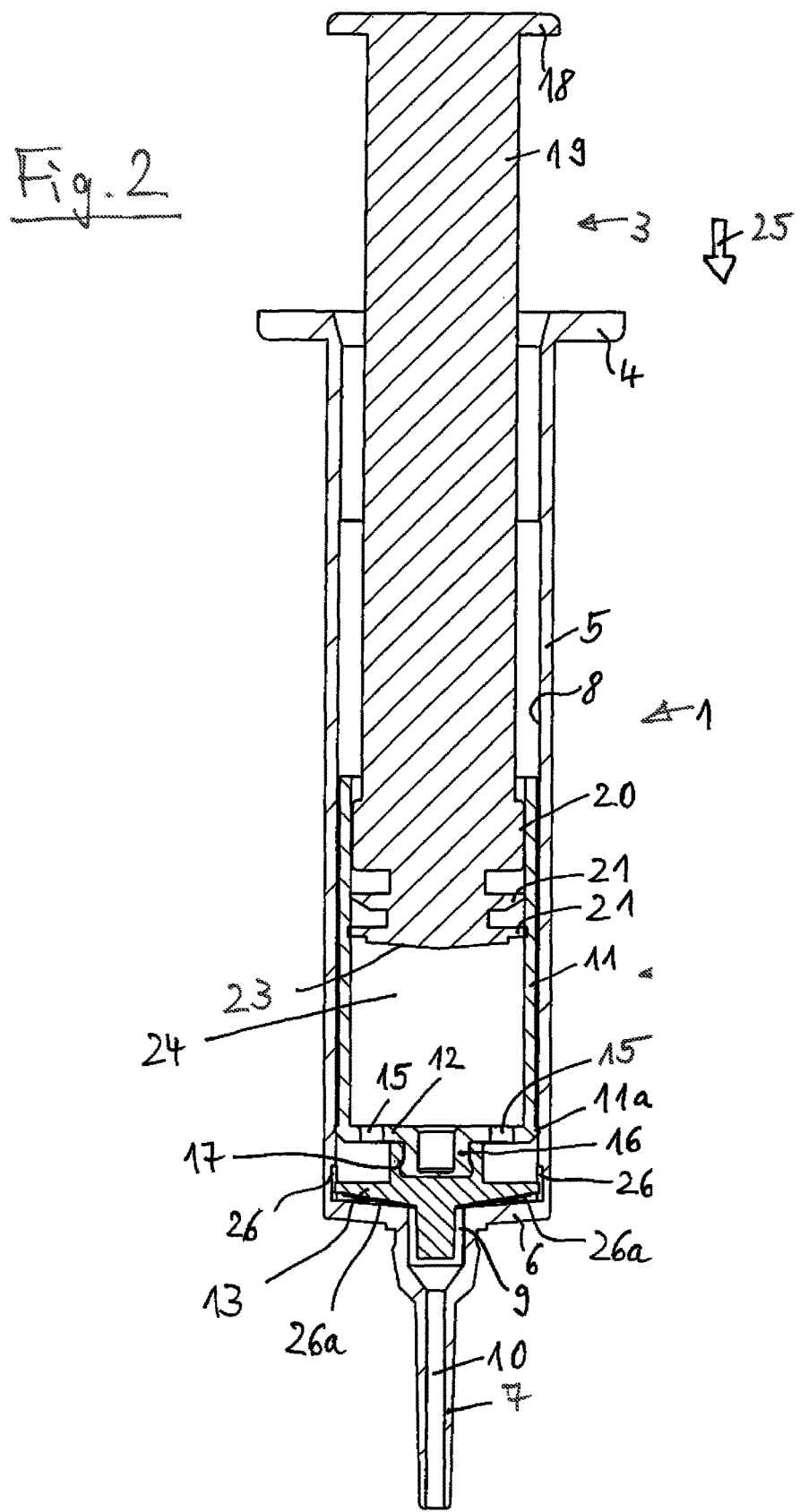
FIG. 2 shows the subject of FIG. 1 after the administering of the first liquid or pasty substance.

This procedure is carried out until the position shown in FIG. 2 is reached in which the cuff 13 is located in the end position in the outer injector body 2. In this lower end position, the cuff 13 contacts the base wall 6 of the outer injector body 1.

The outer injector body 1 has a plurality of channels 26 in its end region. The channels 26 are located in the inner wall 8 of the jacket part 5 of the outer injector body 1. They start at the base wall 6 of the outer injector body 1 and face upwardly from there. They are so long that they project beyond the upper end surface of the cuff 13 when the cuff 13 is in its end position shown in FIGS. 2 and 4. The depth of the channels 26 is furthermore dimensioned such that it is further outwardly in the peripheral direction than the outer diameter of the cuff 13. The channels 26 form a path for flowing around the cuff 13 in this manner. The channels 26 are evenly distributed over the periphery of the jacket part 5 of the outer injector body 1.

The cuff 13 has a plurality of grooves 26a at its lower side. The grooves 26a extend in a radial direction. They extend from inwardly downwardly to outwardly upwardly. The grooves 26a are evenly distributed over the periphery of the cuff 13. It is prevented by the grooves 26a that the lower side of the cuff 13 lies completely and sealingly on the upper border of the administration opening 9. The grooves 26a form a path for flowing around the cuff 13 in this manner.

Figure 3:
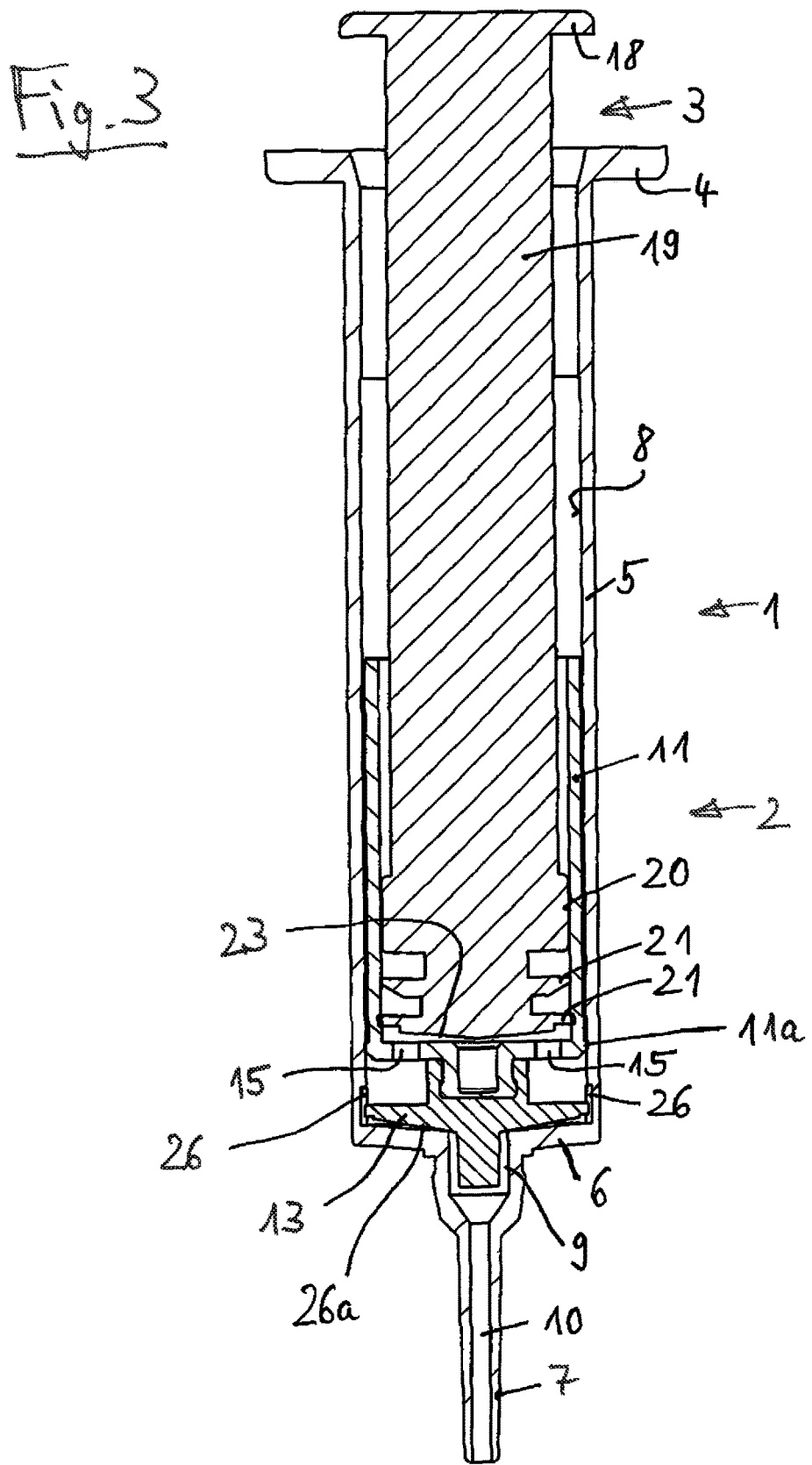
FIG. 3 shows the subject of FIGS. 1 and 2 after the administering of the second liquid or pasty substance.
Figure 4:
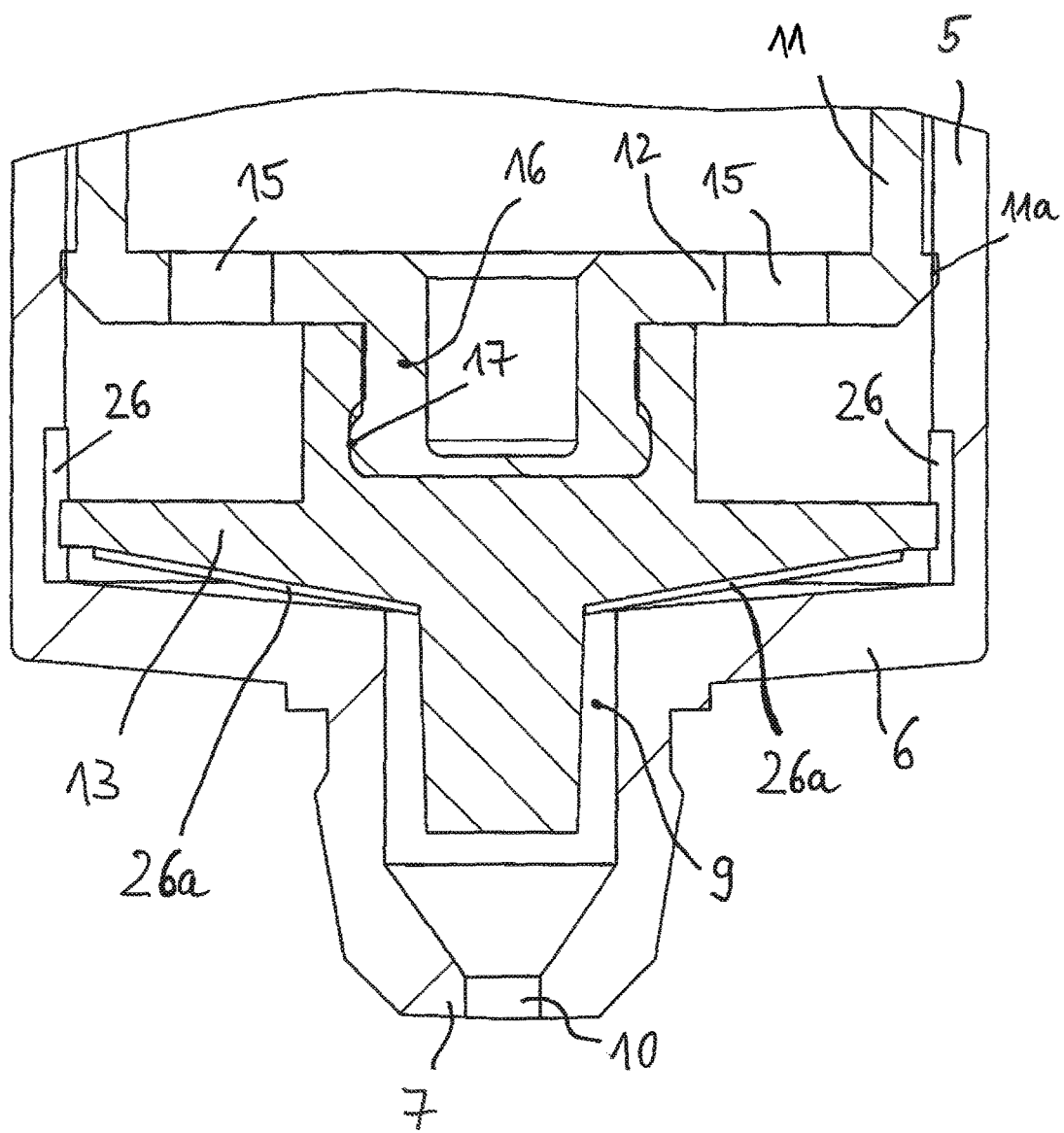
FIG. 4 shows an enlarged detail from FIG. 3.
Figure 5:
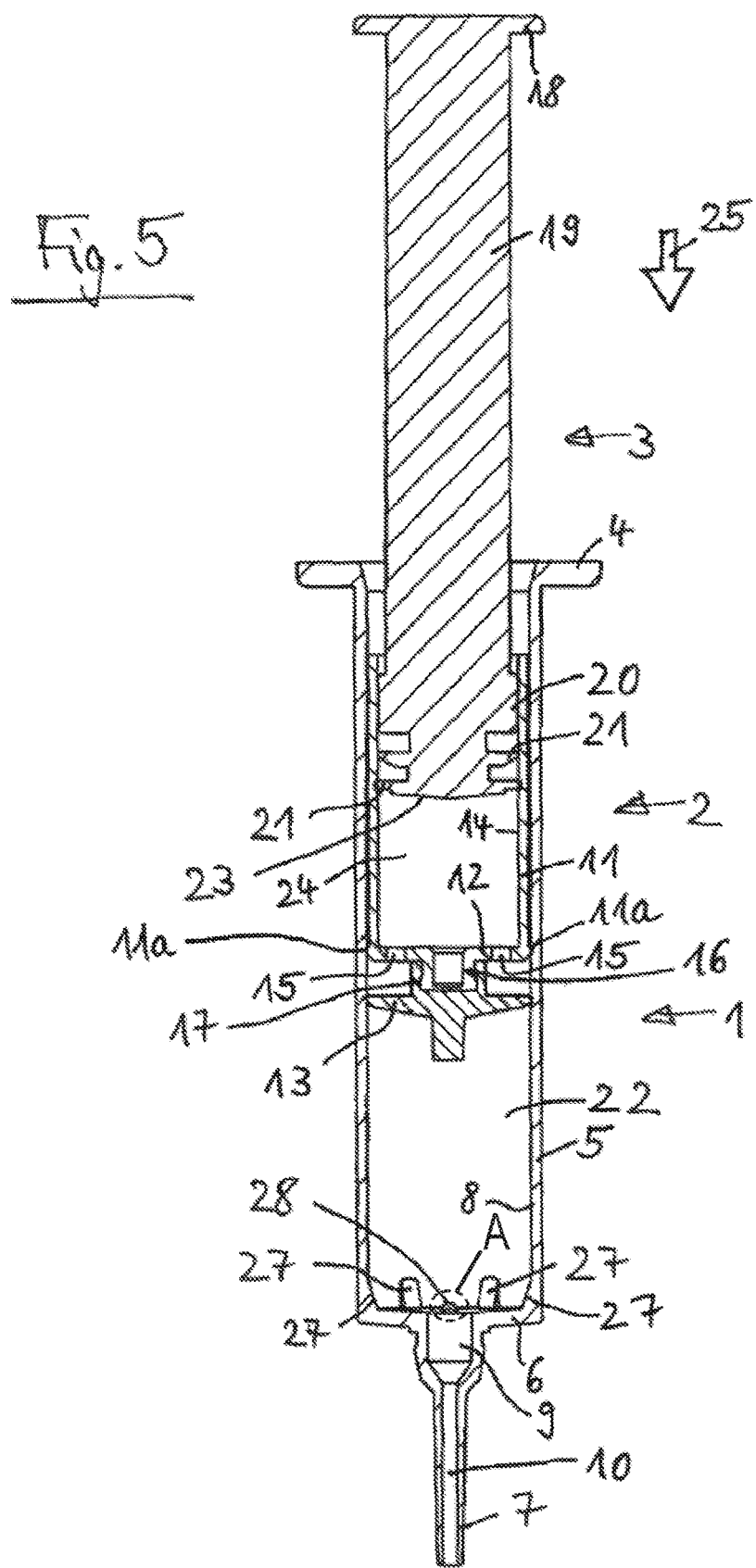
FIG. 5 shows a second embodiment of the present disclosure in the starting position in a lateral sectional view.

When the injector has reached the position shown in FIG. 2, the plunger 3 is moved further downwardly. Its lower end surface 23 moves toward the base wall 12 of the inner injector body 2. The second volume 24 is hereby reduced in size. The second liquid or pasty substance located therein is pressed past the cuff 13 into the administration opening 9 and the administration channel 10 due to this movement through the channels 15 and the channels 26 and the grooves 26a. The movement of the plunger 3 is continued until the end position shown in FIG. 3 is reached in which the lower end surface 23 of the plunger 3 contacts the base wall 12 of the inner injector body 2.

A second embodiment of the injector in accordance with the present disclosure is shown in FIGS. 5 to 8 in which components which are the same are provided with the same reference numerals and will not be described again. The outer injector body 1 has webs 27 in its end region here. The webs 27 are connected to the base wall 6 of the outer injector body 1. They project upwardly from the base wall 6, that is toward the cuff 13. The webs 27 are connected in one piece to the base wall 6. They face from downwardly inwardly to outwardly upwardly. The webs 27 are evenly distributed over the periphery. Six webs 27 are present in the embodiment.

Elevated portions 28 are present between two webs 27. They face upwardly, that is toward the cuff 13. The elevated portions 28 are located in the vicinity of the administration opening 9 in the base wall 6 of the outer injector body 1. The elevated portions 28 are evenly distributed over the periphery. An abutment for the cuff 13 is formed by the elevated portions 28. A lateral sectional view of elevated portions 28 is shown in region A of FIG. 5; FIG. 8 provides an enlarged detail view of region A from a slightly elevated perspective.

Figure 6:
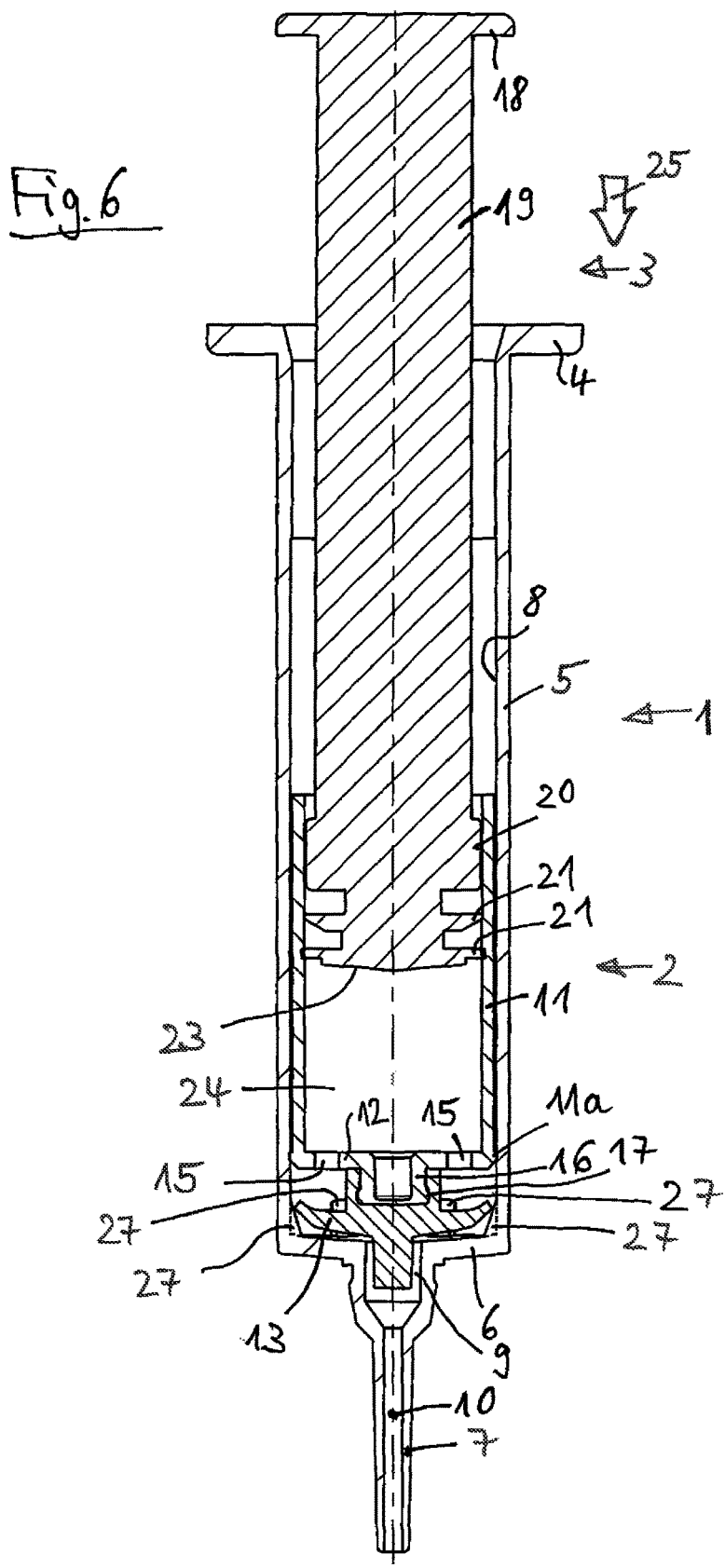
FIG. 6 shows the subject of FIG. 5 after the administering of the first liquid or pasty substance.
Figure 7:
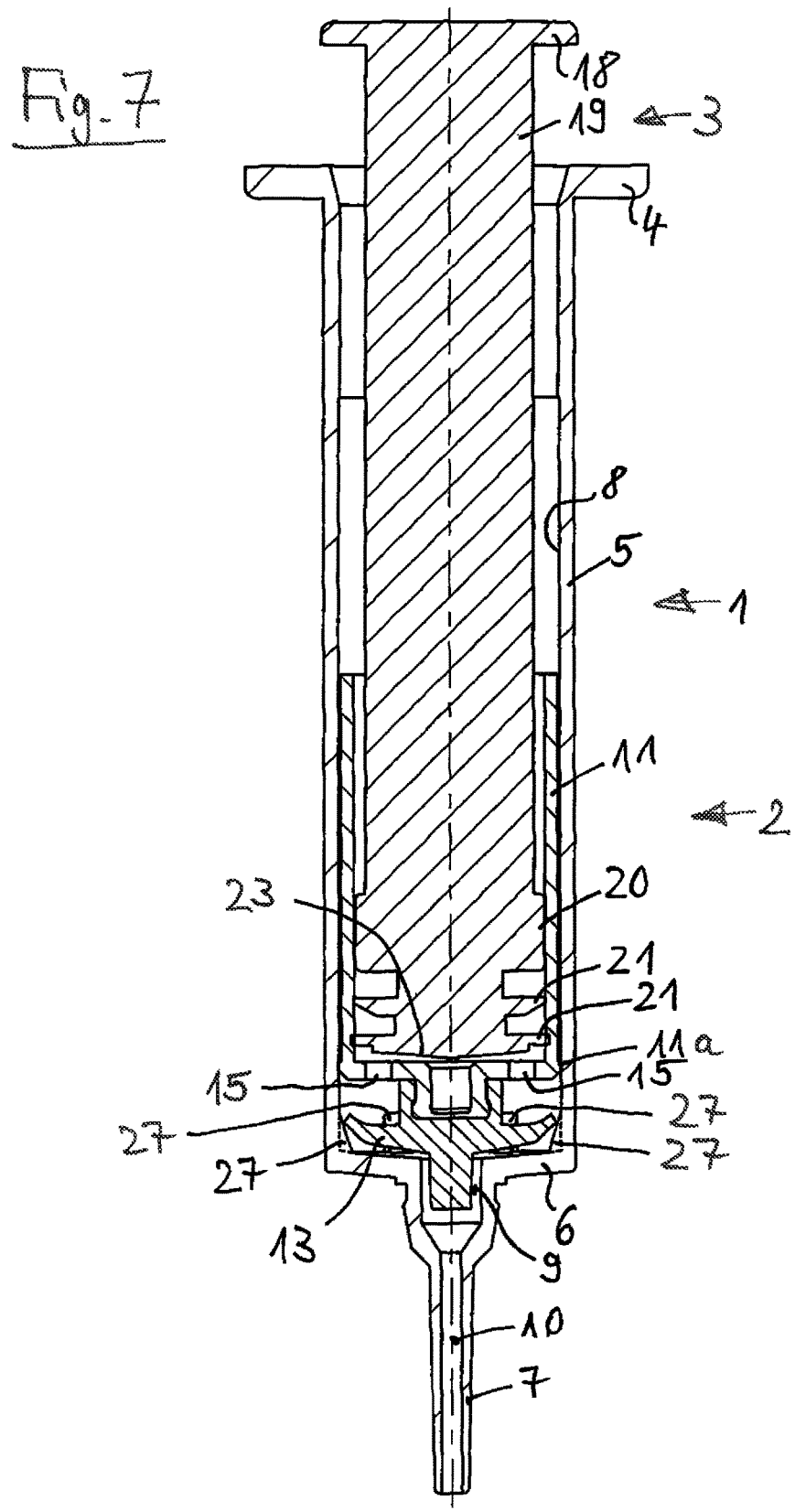
FIG. 7 shows the subject of FIGS. 5 and 6 after the administering of the second liquid or pasty substance.

The cuff 13 is deformable. It is at least deformable in its outer region. When the cuff 13 is moved toward its end position, which is shown in FIGS. 6, 7, and 8, its outer region is upwardly deformed by the webs 27, that is toward the base wall 12 of the inner injector body 2. The outer margin of the cuff 13 is thereby moved away from the inner wall 8 of the outer injector body 1. The cuff 13 thereby no longer sealingly contacts the inner wall 8. It can be flowed around by the second liquid or pasty substance in the regions between the webs 27.

The path of the cuff 13 toward the base wall 6 is bounded by the elevated portions 28 which form an abutment for the lower end surface of the cuff 13. It is thereby ensured that the lower end surface of the cuff 13 does not completely contact the upper border of the administration opening 9 so that the second liquid or pasty substance can flow out of the region of the base wall 6 past the lower end surface of the cuff 13 into the administration opening 9.

A 2-component injector (also called as 2C injector) is provided by the present disclosure by which two different components can be sequentially administered. The two different components are stored separately in the 2C injector, namely in its volumes 22 and 24. They cannot mix or mutually influence one another.

In operation, the inner injector body 2 of the 2C injector is moved in the outer injector body 1 by pressing the plunger 3, whereby the first component is pressed out through the administration channel 10 of the administration spout 7. When the first component has been completely pressed out of the outer injector body 1, the inner injector body 2 is in its end position in the outer injector body 1, as shown in FIGS. 2 and 6. In this end position, the cuff is exposed by channels 26 in the outer injector body 1 in the first embodiment in accordance with FIGS. 1 to 4. The second component can now flow through the channels 15 of the inner injector body 2 and through the channels 26 in the outer injector body 1 and can be pressed out through the administration channel 10 into its administration spout 7.

In the second embodiment in accordance with FIGS. 5 to 8, the end position of the cuff 13 can be formed by the elevated portions 28, which can be formed as webs, in the outer injector body 1. A corresponding free space or channel is formed between the outer injector body 1 and the cuff 13 by the elevated portions 28 or webs. In this end position, the cuff 13 is deformed by webs 27 in the outer injector body 1 such that it leaks. The second component can then move through the channels 15 of the inner injector body 2 and past the deformed, leaking cuff 13 into the outer injector body 1 and can be pressed out through its administration spout 7.

Figure 9:
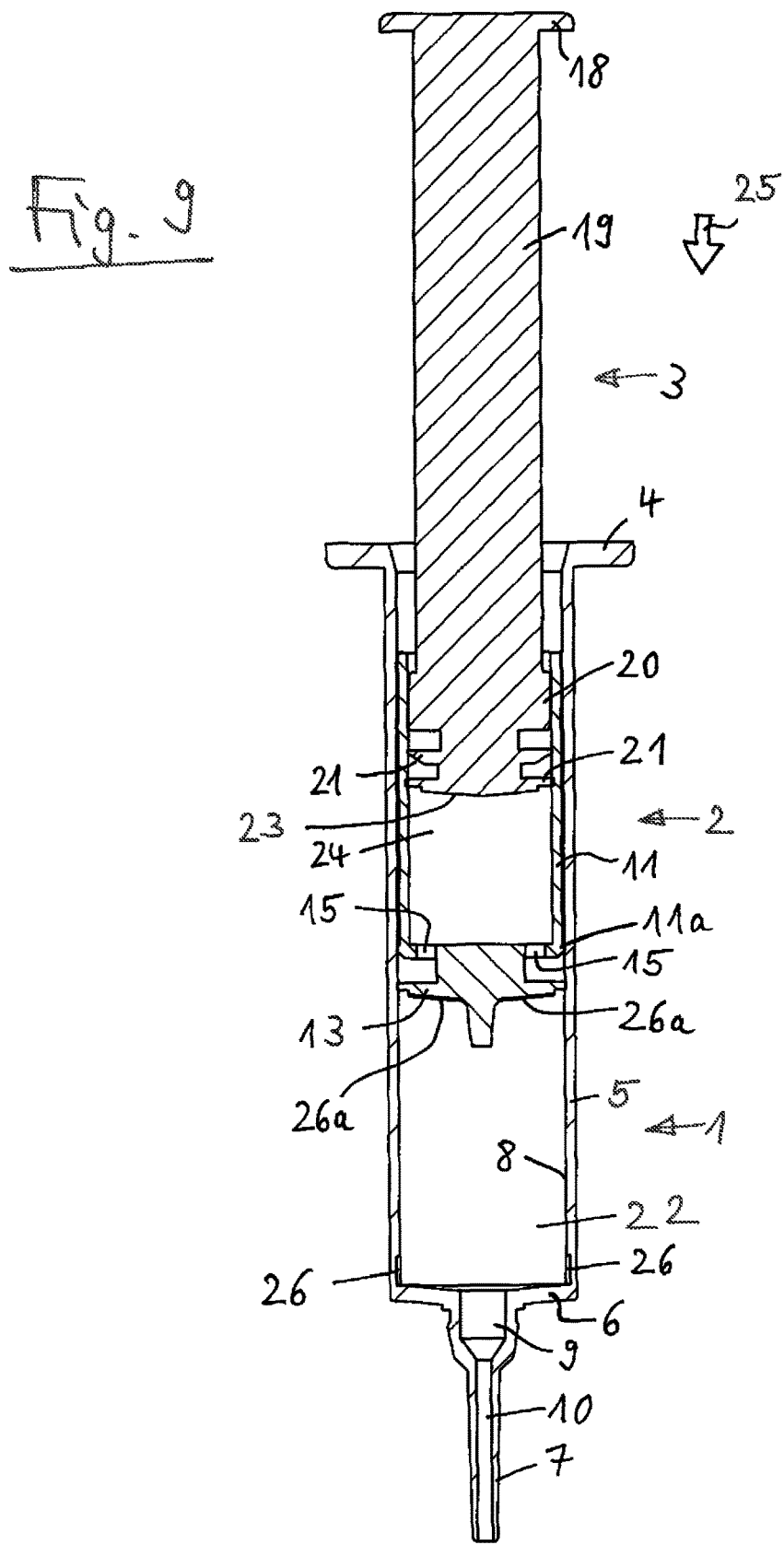
FIG. 9 shows a modified embodiment of the first embodiment of the present disclosure in which the cuff is formed in one piece with the inner injector body.
Figure 10:
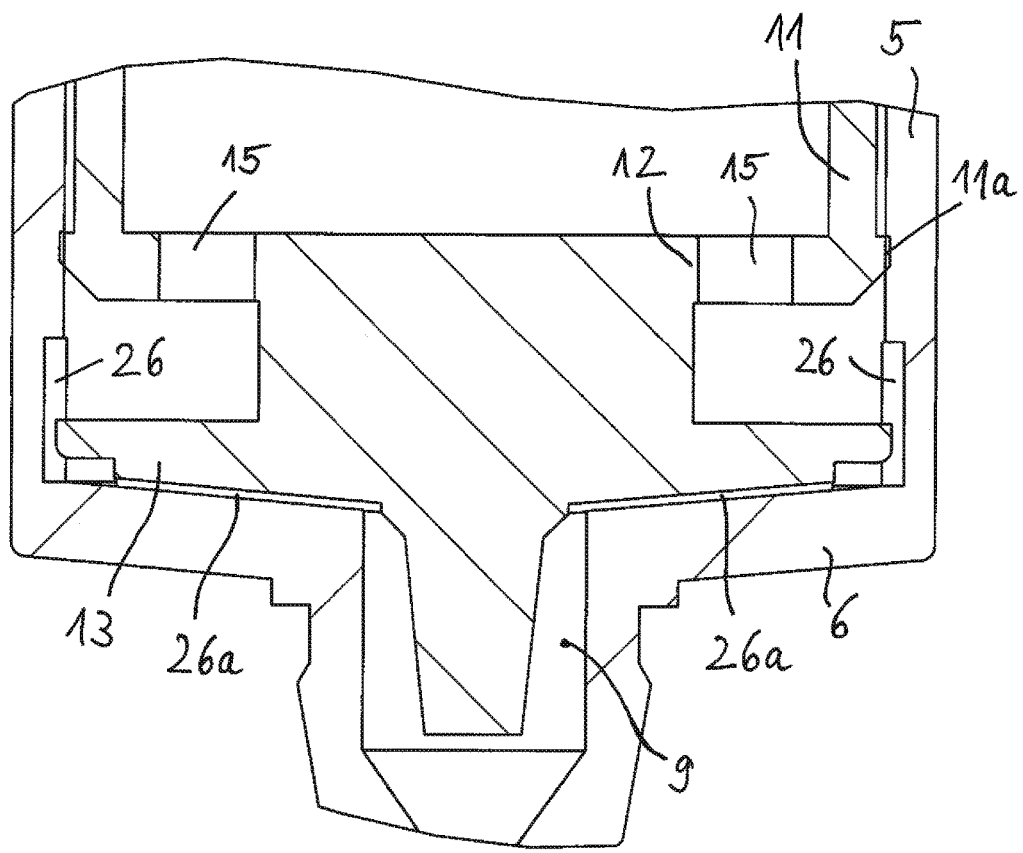
FIG. 10 shows an enlarged detail from FIG. 9.

FIGS. 9 and 10 show a modification of the first embodiment in accordance with FIGS. 1 to 4 in which the cuff 13 is formed in one piece with the inner injector body 2.

In the further modification in accordance with FIG. 11, the cuff 13 is likewise formed in one piece with the inner injector body 2. Here, the channels 15 have a common section 15 and radial sections 15' from the volume 24 to the annular space between the base wall 12 of the inner injector body 2 and the cuff 13. The common section 15 is located at the center of the base wall 12. It extends downwardly in an axial direction there. The radial sections 15' extend from the lower end of the common section 15 outwardly in a radial direction to the mentioned annular space. The embodiment in accordance with FIG. 11 can also be used when the cuff 13 is releasably connected to the inner injector body 2.

Note that the Figures show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

The invention claimed is:

1. An injector for administering a first and a second liquid or pasty substance, the injector comprising:
   an outer injector body in which an inner injector body is longitudinally displaceably guided, the inner injector body in which a plunger is longitudinally displaceably guided;
   wherein the inner injector body comprises a cuff, a jacket, and a base wall, wherein the plunger is longitudinally displaceably guided on an inner wall of the jacket and has a lower end surface facing the base wall of the inner injector body,
   wherein the outer injector body comprises a jacket and a base wall, wherein the inner injector body is longitudinally displaceably guided with the cuff on an inner wall of the jacket of the outer injector body, wherein the cuff has a lower end surface facing the base wall of the outer injector body,
   wherein the cuff comprises an outer rim which sealingly contacts an inner wall of the outer injector body when the cuff is not in an end position in the outer injector body, wherein the outer rim does not contact the inner wall of the outer injector body around its entire circumference when the cuff is in the end position in the outer injector body, and thereby can be flowed around by the second liquid or pasty substance at at least one position where it does not contact the inner wall of the outer injector body, wherein the second liquid or pasty substance flows from a first space formed between the base wall of the inner injector body and the cuff around the outer rim to a second space formed between the base wall of the outer injector body and the lower end surface of the cuff when the cuff is in the end position in the outer injector body, wherein one or more channels are formed in the base wall of the inner injector body which extend axially from an inner volume of the inner injector body to the first space formed between the base wall of the inner injector body and the cuff.

2. The injector of claim 1, wherein an end region of the outer injector body has one or more channels.

3. The injector of claim 1, wherein a lower side of the cuff has one or more grooves.

4. The injector of claim 1, wherein the cuff is deformed in a manner such that it can be flowed around when it is in the end position in the outer injector body.

5. The injector of claim 1, wherein the cuff is releasably connected to the base wall of the inner injector body.

6. The injector of claim 1, wherein the cuff is formed in one piece with the base wall of the inner injector body.

7. The injector of claim 1, wherein one or each of the first and second liquids or pasty substances is a drug.

8. The injector of claim 1, wherein the plunger further comprises a lower seal and an upper seal, wherein the lower seal forms a main seal, and wherein the upper seal forms an additional seal.

9. The injector of claim 3, wherein the one or more grooves extend from inwardly downwardly to outwardly upwardly.

10. The injector of claim 1, wherein the one or more channels have a common section and radial sections, wherein the common section extends downwardly in an axial direction, and wherein the radial sections extend from a lower end of the common section outwardly in a radial direction.

11. The injector of claim 1, wherein the first space is formed between, in an axial direction, the base wall and the cuff of the inner injector body and wherein the base wall and the cuff of the inner injector body extend across a diameter of the outer injector body, the diameter arranged perpendicular to the axial direction.

12. An injector for administering a first and a second liquid or pasty substance, the injector comprising:
an outer injector body in which an inner injector body is longitudinally displaceably guided, the inner injector body in which a plunger is longitudinally displaceably guided;
wherein the inner injector body comprises a jacket and a base wall, wherein the plunger is longitudinally displaceably guided on an inner wall of the jacket and has a lower end surface facing the base wall of the inner injector body,
wherein the inner injector body further includes a cuff which sealingly contacts an inner wall of the outer injector body, and which can be flowed around by the second liquid or pasty substance when it is in an end position in the outer injector body,
wherein a space is formed between the base wall and the cuff of the inner injector body, and one or more channels are formed in the base wall which extend axially from an inner volume of the inner injector body to the space formed between the base wall and the cuff; and
a plurality of webs evenly distributed around a periphery of an end region of the outer injector body, wherein the webs face from downwardly inwardly to outwardly upwardly; and at least one elevated portion in a base wall of the outer injector body, between the webs, the at least one elevated portion extending upwardly toward the cuff from the base wall of the outer injector body.

13. The injector of claim 12, wherein the at least one elevated portion faces upwardly toward the cuff, and wherein the plurality of webs project upwardly from the base wall and inwardly from the inner wall toward the cuff.

14. The injector of claim 12, wherein the at least one elevated portion forms an abutment for a lower end surface of the cuff.

* * * * *